(12) United States Patent
Goerne et al.

(10) Patent No.: US 9,314,550 B2
(45) Date of Patent: Apr. 19, 2016

(54) IMPLANT MATRIX MADE OF A POLYMER MIXTURE

(71) Applicant: Bioenergy Capital AG, Cologne (DE)

(72) Inventors: Martin Goerne, Hamburg (DE); Thomas Kordick, Goldbach (DE)

(73) Assignee: BIOENERGY CAPITAL AG, Cologne (DE)

( * ) Notice: Subject to any disclaimer, the term of this patent is extended or adjusted under 35 U.S.C. 154(b) by 0 days.

(21) Appl. No.: 14/376,132

(22) PCT Filed: Feb. 1, 2013

(86) PCT No.: PCT/EP2013/000325
§ 371 (c)(1),
(2) Date: Jul. 31, 2014

(87) PCT Pub. No.: WO2013/113515
PCT Pub. Date: Aug. 8, 2013

(65) Prior Publication Data
US 2015/0004638 A1    Jan. 1, 2015

(30) Foreign Application Priority Data
Feb. 1, 2012 (EP) ..................................... 12000651

(51) Int. Cl.
| | |
|---|---|
| *A61L 27/26* | (2006.01) |
| *A61L 27/56* | (2006.01) |
| *A61L 27/58* | (2006.01) |
| *A61L 27/34* | (2006.01) |
| *A61L 27/54* | (2006.01) |

(52) U.S. Cl.
CPC ................ *A61L 27/26* (2013.01); *A61L 27/34* (2013.01); *A61L 27/54* (2013.01); *A61L 27/56* (2013.01); *A61L 27/58* (2013.01); *A61L 2430/00* (2013.01); *Y10T 428/249992* (2015.04)

(58) Field of Classification Search
IPC ................... A61L 27/26,27/18, 27/34
See application file for complete search history.

(56) References Cited

U.S. PATENT DOCUMENTS

| | | |
|---|---|---|
| 5,522,895 A | 6/1996 | Mikos |
| 7,618,646 B2 | 11/2009 | Goerne et al. |
| 8,828,546 B2 | 9/2014 | Dias et al. |
| 2005/0042253 A1 | 2/2005 | Farrar et al. |
| 2007/0166343 A1 | 7/2007 | Goerne et al. |
| 2007/0231365 A1* | 10/2007 | Wang et al. .................... 424/426 |
| 2009/0130699 A1 | 5/2009 | Goerne et al. |
| 2010/0028405 A1 | 2/2010 | Goerne et al. |
| 2011/0059874 A1 | 3/2011 | Rooijmans et al. |

FOREIGN PATENT DOCUMENTS

| | | |
|---|---|---|
| EP | 1264607 A1 | 12/2002 |
| EP | 1185621 B1 | 2/2010 |
| EP | 1656166 B1 | 11/2011 |
| JP | 2003024340 A | 1/2003 |
| JP | 2003503318 A | 1/2003 |
| JP | 2007503226 A | 2/2007 |
| JP | 2007527435 A | 9/2007 |
| JP | 2010506828 A | 3/2010 |
| JP | 2011513566 A | 4/2011 |
| WO | 0078928 A2 | 12/2000 |
| WO | 2004108810 A1 | 12/2004 |
| WO | 2006061229 A1 | 6/2006 |

OTHER PUBLICATIONS

Pistner et al., Poly(l-lactide): a long-term degradation study in vivo. I. Biological results, Biomaterials 14(9):671-677, 1993.*
Lee et al., "Elastic biodegradable poly(glycolide-co-caprolactone) scaffold for tissue engineering," J Biomed Materials Res Part A 66A(1):29-37, 2003.s.*
Japanese Office Action dated Jan. 20, 2015 issued in corresponding Japanese Application No. 2014-555127.

* cited by examiner

*Primary Examiner* — Rosanne Kosson
(74) *Attorney, Agent, or Firm* — Morris & Kamlay LLP

(57) ABSTRACT

A porous implant matrix consists mainly of a mixture of polymers which are differently rapidly degradable, wherein nominal resorption times of two of the components of the mixture, each accounting for at least 10% of the mixture, differ by a factor of at least 5. The porous implant matrix is manufactured from a mixture of the at least two differently rapidly degradable polymers, wherein particles of both polymers are mixed with particles of a water-soluble solid and a solvent for one of the polymers, and after evaporating the solvent is optionally compacted, and the solid is removed by watering.

13 Claims, No Drawings

IMPLANT MATRIX MADE OF A POLYMER MIXTURE

BACKGROUND OF THE INVENTION AND FIELD OF THE INVENTION

The present application relates to porous matrices for surgical purposes.

Cell implants on the basis of porous matrices made of bio-acceptable polymers are known from WO 2004/108810 A1. In such matrices, the pores are interconnected and serve as template for the infiltration of cells in vivo (e. g. therapeutic) or in vitro (e.g. diagnostic). For transplantations, such a bio-resorbable matrix may serve to temporally localise the transplant, and as a placeholder for gradually forming tissue.

The known templates are, in some applications, not yet fully satisfying, in particular as regards the clinical performance.

SUMMARY OF THE INVENTION

The invention aims at improving the clinical performance of the templates.

To this end, the invention proposes a porous template made from a mixture of differently rapidly degradable polymers, wherein nominal resorption times of two of the components of the mixture, each accounting for at least 10% of the mixture, differ by a factor of at least 5. Without limitation to the conjectured mode of action, the inventors assume that the more rapidly resorbed polymer gradually creates spaces for forming vessels, while the integrity of the overall structure is secured by the more slowly resorbed polymer, without individual structure elements acting as foreign bodies. Additionally, the progressing degradation of the more rapidly resorbing polymers changes the physiologic environment in a manner beneficial for the therapeutic success.

According to a further aspect, the invention proposes methods for the manufacture or porous bioresorbable matrices, wherein a mixture of at least two differently rapidly resorbable polymers and a water soluble pore forming agent and a solvent for one of the polymers is formed, followed by evaporating the solvent and watering to form the pores. In variants, the mixture is compacted after evaporating the solvent. Both methods result in highly porous polymer matrix disks, the clinical performance of which is excellent. The degradation times of the polymers differ by a factor of 5 or more.

In embodiments, the porous matrix is hydrophilically coated, e.g. with polymerized (meth)acrylic acid. To this end, a plasma coating step is followed by a plasma-less coating step, whereby the required layer thicknesses of above one mikrometer are achieved. The coating results in further improvement of the cell adhesion.

DETAILED DESCRIPTION OF THE INVENTION

Further features of the invention are available from the following description of embodiments in conjunction with the claims and the drawings. The invention is not defined by the described embodiments, but by the scope of the accompanying patent claims. In particular, individual features of embodiments of the invention can be realized in a different number and combination than in the examples following hereunder.

In a main application, matrices are provided for covering a defect, for example a hernia dehiscence. It is envisioned that a first part of the employed polymer mixture is degraded more rapidly and another part of the polymer mixture erodes more slowly (ratio of the degrading times at least 5) and secures the structural integrity for a longer time, e.g. 2,5-3 years (or at least 2 and/or less than 5 years). By the gradual dissolution of the more rapidly degradable part of the matrix within 3-4 months, or at least 2 and/or less than 7 months, the physiologic environment is influenced in a manner beneficial for the therapeutic success. Such polymers are desirably based on α-hydroxycarbonic acids such as lactic acid and/or glycolic acid, e. g. PLA or PLGA. The manufacturers of such polymers certified for use in the human body indicate the nominal degradation times relevant here. The polymers employed herein are available e.g. from Evonik and bear the designations L210s, L210, L09s, L207s, L206s (more slowly degradable PLGA-polymers) or RG502, RG502H, RG505 (more rapidly degradable PLGA-polymers), respectively.

In the main variant, the matrices according to the invention are made sufficiently mechanically stable, that they withstand e.g. the strain due to surgical suturing processes. At their periphery, the matrices can thereby be connected to body tissue. Their porosity ensures that the matrices are infiltrated with connective tissue cells. A particulalry good adhesion is achieved by a coating with PAA in a combined PECVD/CVD-process, in which an initial plasma-generated layer serves as an adhesive for a subsequent crystalline PAA-layer. According to an embodiment, the matrix has a pore-reduced or pore-frei side, which provides for the actual covering, and a pore-rich side, which is beneficial for the infiltration. In the body, the more smooth pore-reduced side may be arranged towards the body's interior, in order not to provide an area of attack in case of the application of pressure by the body organs onto the site of the defect.

In a variant, the matrix is infiltrated in advance for example with hepatocytes and/or with islet-of-Langerhans cells. Such biochemically functional cells adhere to the inner walls of the pores of the foam-like matrix (adhesion rates over 80% or, when suitably coated, over 95%) and may be transplanted with the matrix into mesothelial pockets, ideally of the cell donor itself. Herein it is exploited that in this case, no rejection reaction occurs, but only a comparatively mild foreign body stimulation, which is even beneficial for the therapeutic process. Within a few weeks, the matrix is vascularised and the implanted cells are no more dependent only on diffusive supply. The matrices are arranged so that the pore-reduced (or pore-free) side is inwards and the pore-rich side is outwards, to maintain the loss rate due to emigration to a low level.

As mentioned above, particularly good adhesion rates are observed with coated matrices, namely ones which are initially plasma coated, in a combined PECVD/CVD-process, with a thin PAA-layer (e.g. 20-30 nm) and are subsequently coated with a thicker PAA-layer (e.g. 20-30 μm) without the action of a plasma. This upper layer forms a crystalline, hydrophilic layer.

Initially, in an embodiment a solution of one of the employed polymers in chloroform certified for medicinal purposes is poured into a mold and the solvent evaporated at 45°-65° C. Next, a polymer mixture having a pre-defined particle size distribution is mixed with a rock salt granulate likewise having a pre-defined particle size distribution, is admixed with a solution of one of the polymers in chloroform and then brought onto the polymer layer already present. From this pre-form, the solvent evaporates at slightly elevated temperature (45-65° C.) and same can be compacted by the application of pressure if desired. Subsequently, the pre-form is watered to remove the salt and thereby provide the desired porosity. Herein, the initially manufactured polymer layer remains pore-free. According to the field of use, the thickness of the pore-reduced layer can be controlled by the amount and concentration of the initial solution. For example, a sturdy membrane is obtained if, for a concentration of the solution of e.g. 4% in chloroform (slowly degradable polymer) the filling level is about 5-50 mm, typically 20-25 mm. The evaporating of the chloroform takes about 1,5 h and results in a layer thickness of ca. 0,5-2 mm. In the other case, for the same polymer concentration, one starts out from a filling level of only 0,1-0,5 mm, whereby the evaporating of the chloroform is completed earlier (ca. 20-30 min), and the resulting membrane has a thickness of only ca. 10-20 µm.

The rock salt particles of the pore-forming mixture are somewhat more coarse (median at 400-420 µm) than the polymer particles (median of the more slowly degradable polymer between 210 µm and 230 µm, that of the more rapidly degradable polymer between 150 µm and 170 µm). Herein, the distribution widths (5%/95%) are similar, namely around ±85-95 µm for salt or total polymer, respectively. The shape of the distribution can be bi- or tri-modal. The composition of the stratifying mixture is about 96% salt, 1-1,5% solid polymer and a further ca. 3-5% dissolved polymer, wherein the volume proportions of solids and liquids are about equal. In total, the proportion of the rapidly degradable polymer is only about 5-20% of the polymers. The total thickness of the pore forming layer is 4-5 mm. In the variant of a more fragile initial layer, the salt can be selected somewhat finer (median ca. 350-370 µm). In this case, the total thickness of the pore forming layer is 5-6 mm. The watering takes about 24 h and is followed by drying at 45-50° C. When a coating is made, the matrix is placed with its pore-reduced side (if present) down and thus mainly the open pore side is coated.

In an application outside of the body, a matrix according to the description above may serve to fix cells which are exposed to an agent in a bioreactor. For example, in this manner defined cell types may be studied with regard to whether they respond to a medicament at issue or not, and the therapy can be planned in dependence of the observation results obtained thereby. Likewise, the development of medicaments may be simplified, because any toxicity is recognized at an early stage.

The skilled person will realize that alterations of the examples described above are possible which come within the scope of the appended claims.

The invention claimed is:

1. A porous implant matrix, mainly comprising a mixture of differently rapidly resorbable polymers, wherein nominal resorption rates of two of the mixture polymers, each accounting for at least 10% of the mixture, differ by a factor of at least 5, wherein the porous matrix comprises a surface hydrophilically coated with poly(acrylic acid), PAA, wherein a PAA layer thickness initially applied under the influence of a plasma is less than a PAA layer thickness subsequently applied without action of the plasma, wherein the porous matrix has a connective porosity of at least 80%.

2. The porous implant matrix of claim 1, wherein the mixture polymers are poly((α-hydroxy)carboxylic acids).

3. The porous implant matrix of claim 2, wherein the mixture polymers are poly(lactic acid) (PLA) and poly(lactic-co-glycolic acid) (PLGA).

4. The porous implant matrix of claim 1, wherein the hydrophilic surface comprises acrylic acid units.

5. The porous implant matrix of claim 1, wherein a nominal resorption time of the more rapidly resorbable polymer is less than 4 months.

6. The porous implant matrix of claim 1, wherein a nominal resorption time of the more slowly resorbable polymer is more than 20 months.

7. The porous implant matrix of claim 1, further comprising viable cells.

8. The porous implant matrix of claim 7, further comprising test agent.

9. A process for manufacturing the porous implant matrix of claim 1 comprising the steps of:
  a) mixing particles of both polymers with particles of a water soluble solid and a solution of at least one of the at least two differently resorbable polymers in a non-water-miscible solvent,
  b) removing the water soluble solid by watering, thereby creating pores in the matrix made up of the at least two differently resorbable polymers, and
  c) coating the porous matrix with a hydrophilic material after the watering, wherein the PAA-plasma coating step is followed by the PAA-coating step without plasma, such that the PAA layer thickness applied initially under the influence of the plasma is less than the PAA layer thickness applied without the action of the plasma.

10. The process of claim 9, comprising applying pressure for compacting the mixture after evaporating the solvent and before the watering.

11. The process of claim 9, wherein chloroform is used as the solvent.

12. The process of claim 9, wherein a precursor of the hydrophilic material is acrylic acid or acrylic acid anhydride.

13. The process of claim 9, further comprising infiltrating porous implant the matrix with viable cells outside of the body, and exposing the cells to a predetermined test agent.

* * * * *